United States Patent [19]
Miura et al.

[11] Patent Number: 6,114,277
[45] Date of Patent: Sep. 5, 2000

[54] PROCESS FOR PREPARING CYANO GROUP-CONTAINING AROMATIC METHYLAMINES

[75] Inventors: Motoo Miura; Yuseki Suyama; Hideyuki Kondo; Kouhei Morikawa, all of Kawasaki, Japan

[73] Assignee: Showa Denko K.K., Tokyo, Japan

[21] Appl. No.: 09/155,450

[22] PCT Filed: Feb. 4, 1998

[86] PCT No.: PCT/JP98/00464

§ 371 Date: Sep. 30, 1998

§ 102(e) Date: Sep. 30, 1998

[87] PCT Pub. No.: WO98/33767

PCT Pub. Date: Aug. 6, 1998

[30] Foreign Application Priority Data

Feb. 4, 1997 [JP] Japan .................... PCT/JP97/00270

[51] Int. Cl.[7] .......................... B01J 25/02; C07C 255/00
[52] U.S. Cl. ........................................... 502/301; 558/422
[58] Field of Search ................ 502/301; 558/422

[56] References Cited

U.S. PATENT DOCUMENTS 5,151,543  9/1992  Ziemecki .

FOREIGN PATENT DOCUMENTS

| 40-10133 | 5/1940 | Japan . |
| 49-85041 | 8/1974 | Japan . |
| 6-507909 | 9/1994 | Japan . |
| 7-502040 | 3/1995 | Japan . |
| 9-040630 | 2/1997 | Japan . |

*Primary Examiner*—Cecilia Tsang
*Assistant Examiner*—Joseph Murray
*Attorney, Agent, or Firm*—Sughrue, Mion, Zinn, Macpeak & Seas, PLLC

[57] ABSTRACT

The object of the invention is to provide a process for preparing a cyano group-containing methylamine, comprising hydrogenating only one of the two nitrile groups of a aromatic dinitrile, wherein the aromatic dinitrile is reacted a a high conversion ratio using a small amount of a catalyst under the conditions of a low temperature and a low pressure to prepare a cyano group-containing aromatic methylamine in a high yield.

19 Claims, No Drawings

PROCESS FOR PREPARING CYANO GROUP-CONTAINING AROMATIC METHYLAMINES

FIELD OF THE INVENTION

The present invention relates to a process for preparing cyano group-containing aromatic methylamines, and more particularly to a process for preparing cyano group-containing aromatic methylamines in high yields, which comprises efficiently converting an aromatic dinitrile using a small amount of a catalyst under the conditions of a low temperature and a low pressure.

BACKGROUND OF THE INVENTION

Cyano group-containing aromatic methylamines are useful as starting materials or intermediate products for producing pharmaceuticals, agricultural chemicals, polymer additives and other organic compounds. For example, by hydrolyzing m- or p-cyanobenzylamine, the corresponding useful m- or p-aminomethylbenzoic acid can be easily obtained.

By the way, in order to obtain cyano group-containing aromatic methylamines by the addition of hydrogen to only one of the two nitrile groups of an aromatic dinitrile, there is a process described in Japanese Patent Laid-Open Publication No. 85041/1974. In this process, a catalyst comprising a carrier and palladium supported thereon is used as a catalyst, but it is essential to add liquid ammonia and an inorganic alkali, and besides the reaction is conducted at a high pressure of 200 kg/cm$^2$.

National Publication of International Patent No. 507909/1994 discloses a process for preparing an aminonitrile, wherein only one of nitrile groups of an aliphatic dinitrile is hydrogenated using Raney nickel or Raney cobalt as a catalyst. In this process, however, there is no description on an aromatic dinitrile, and there resides a defect such that increase of a conversion ratio of the aliphatic dinitrile causes lowering of selectivity to the aminonitrile.

National Publication of International Patent No. 502040/1995 discloses a process for preparing an aminonitrile by partial hydrogenation of a nitrile compound having two or more nitrile groups. In this process, Raney nickel having been pretreated with an alkanolate such as sodium methoxide is used as a catalyst. This process, however, has problems such that dehydration of a solvent is substantially essential, a high pressure of 70 atm is necessary, and an alkanolate that is relatively expensive and inconvenient in handling must be used.

The present inventors attempted hydrogen addition reactions of aromatic dinitriles in the presence of conventional Raney catalysts containing nickel and/or cobalt with variously selecting a reaction temperature, a hydrogen pressure, a solvent, and a reaction time and an amount of the catalyst. As a result, when the amount of the catalyst was small, the conversion ratio of the aromatic dinitrile as a starting material was low, and the cyano group-containing aromatic methylamine could not be prepared in a sufficient yield. Further, with increase of the amount of the catalyst, the conversion ratio was increased, but simultaneously, two nitrile groups of the aromatic dinitrile were both hydrogenated to increase production of a diamine, and hence the yield of the aimed cyano group-containing aromatic methylamine was hardly increased.

Thus, it was difficult to conduct hydrogenation reaction of an aromatic dinitrile at a high conversion ratio and to prepare only a cyano group-containing aromatic methylamine in a high yield, even though the conventional Raney nickel containing nickel and/or cobalt was used as it was.

In such circumstances, the present inventors have earnestly studied to obtain catalysts capable of performing reaction of the aromatic dinitrile at a high conversion ratio and thereby preparing a cyano group-containing aromatic methylamine in a high yield. As a result, they have found that a Raney catalyst having been subjected to a specific treatment is effective, and have accomplished the present invention.

OBJECT OF THE INVENTION

The present invention is intended to solve such problems associated with the prior art as described above, and it is an object of the invention to provide a process for preparing a cyano group-containing aromatic methylamine from an aromatic dinitrile, comprising hydrogenating only one of two nitrile groups of the aromatic dinitrile, wherein the aromatic dinitrile is subjected to hydrogen addition reaction at a high conversion ratio using a small amount of a catalyst under the conditions of a low temperature and a low pressure to prepare the cyano group-containing aromatic methylamine in a high yield.

SUMMARY OF THE INVENTION

The present invention is characterized in that, in the preparation of a cyano group-containing methylamine from an aromatic dinitrile, a Raney catalyst activated by bringing it into contact with hydrogen in a solvent (activated Raney catalyst) is used as a catalyst.

The present invention is characterized in that a Raney catalyst having been used in the preparation of a cyano group-containing aromatic methylamine from an aromatic dinitrile is brought into contact with hydrogen in a solvent in the presence of an alkali to regenerate the Raney catalyst, and is further characterized in that the catalyst thus regenerated (regenerated Raney catalyst) is used in the preparation of a cyano group-containing aromatic methylamine from an aromatic dinitrile.

In the present invention, it is desired that the activated Raney catalyst is used in an amount of 0.1 to 10% by weight, preferably 0.5 to 5% by weight, based on the aromatic dinitrile, and/or the regenerated Raney catalyst is used in an amount of 0.1 to 50% by weight, preferably 0.5 to 20% by weight, based on the aromatic dinitrile.

In the present invention, the activation of a Raney catalyst is desirably conducted by bringing a Raney catalyst into contact with hydrogen under the conditions of a temperature of room temperature to 200° C. and a hydrogen partial pressure of 0.1 to 50 kg/cm$^2$, and the regeneration of a Raney catalyst is desirably conducted by bringing a Raney catalyst into contact with hydrogen under the conditions of a temperature of room temperature to 200° C. and a hydrogen partial pressure of 0.1 to 50 kg/cm$^2$ in the presence of an alkali in an amount of 0.1 to 100% by weight based on the Raney catalyst subjected to the regeneration.

In the process for preparing a cyano group-containing aromatic methylamine from an aromatic dinitrile according to the invention, at least one of iron, iron oxide and iron hydroxide is desirably allowed to be present together with the activated Raney catalyst and/or the regenerated Raney catalyst.

In the present invention, it is desired that at least one of iron, iron oxide and iron hydroxide is used in the total amount of 0.1 to 100% by weight based on the Raney catalyst.

In the present invention, the Raney catalyst is preferably a Raney catalyst containing nickel and/or cobalt, more preferably Raney nickel or modified Raney nickel.

In the present invention, the solvent is preferably a solvent containing an alcohol, more preferably methanol.

In the present invention, the aromatic dinitrile is preferably phthalonitrile, isophthalonitrile or terephthalonitrile.

According to the process for preparing a cyano group-containing aromatic methylamine of the present invention which comprises hydrogenating only one nitrile group (N≡C—) of two nitrile groups of the aromatic dinitrile, the aromatic dinitrile is subjected to hydrogen addition reaction at a high conversion ratio under the conditions of a low temperature and a low pressure using a catalyst in an amount smaller than that of a conventional one, whereby the cyano group-containing aromatic methylamine can be prepared in a high yield.

DETAILED DESCRIPTION OF THE INVENTION

The process for preparing a cyano group-containing aromatic methylamine according to the invention is described in detail hereinafter.

In the process for preparing a cyano group-containing aromatic methylamine from an aromatic dinitrile according to the invention, at least one of the following catalysts (a) and (b) is used as a catalyst;

(a) a Raney catalyst activated by bringing it into contact with hydrogen in a solvent (sometimes referred to as "activated Raney catalyst" hereinafter), and (b) a Raney catalyst regenerated by bringing a Raney catalyst having been used for preparing a cyano group-containing aromatic methylamine from an aromatic dinitrile into contact with hydrogen in a solvent (sometimes referred to as "regenerated Raney catalyst" hereinafter).

In the preferred embodiment, the activated Raney catalyst is used in an amount of 0.1 to 10% by weight, preferably 0.5 to 5% by weight, based on the aromatic dinitrile, and the regenerated catalyst is used in an amount of 0.1 to 50% by weight, preferably 0.5 to 20% by weight, based on the aromatic dinitrile.

Activation Treatment and Regeneration Treatment of Raney Catalyst

In the present invention, the "Raney catalyst" to be activated by contact with hydrogen in a solvent is a porous metallic catalyst having a large specific surface area, which is obtained by removing a part of components from an alloy of two or more metals.

More specifically, the Raney catalyst is a porous metallic catalyst obtained by eluting an alkali- or acid-soluble metal from an alloy of an alkali- or acid-insoluble metal (e.g., nickel, cobalt or both of them) and an alkali- or acid-soluble metal (e.g., aluminum, silicon, zinc or magnesium) in an alkali or an acid.

Of such Raney catalysts, preferably used is a Raney catalyst containing nickel, cobalt or both of them, and more preferably used is a nickel-containing Raney catalyst.

In the present invention, also employable is a modified Raney catalyst obtained by modifying a Raney catalyst in the presence of a metal except for nickel and cobalt or in the presence of a metallic oxide except for nickel oxide and cobalt oxide. The modified Raney nickel is, for example, a Raney nickel having been modified with iron and/or chromium.

In the present invention, activation of the Raney catalyst is preferably carried out by treating the Raney catalyst in a solvent and in a hydrogen atmosphere.

On the other hand, the Raney catalyst to be regenerated by contact with hydrogen in a solvent is a recovery of the above activation of the Raney catalyst which is used for preparing a cyano group-containing methylamine from an aromatic dinitrile.

In the present invention, Regeneration of the Raney catalyst is preferably carried out by treating the Raney catalyst in a solvent, in the presence of an alkali, and in a hydrogen atmosphere.

In the activation treatment and the regeneration treatment, the hydrogen partial pressure is in the range of usually 0.05 to 100 kg/cm$^2$, preferably 0.1 to 50 kg/cm$^2$, and the temperature of the system is in the range of usually 0 to 250° C., preferably room temperature (i.e., 15 to 25° C.) to 200° C. If the hydrogen partial pressure is less than 0.1 kg/cm$^2$, particularly less than 0.05 kg/cm$^2$, or if the temperature is lower than room temperature, particularly lower than 0° C., the effects of the activation treatment (hydrogen treatment) and the regeneration treatment are lowered. If the hydrogen partial pressure is more than 50 kg/cm$^2$, particularly more than 100 kg/cm$^2$, or if the temperature is higher than 200° C., particularly higher than 250° C., a diamine wherein two nitrile groups of the aromatic diamine are both hydrogenated is produced in a large amount, or the activity of the catalyst is lowered, whereby the yield of the cyano group-containing aromatic methylamine may be decreased.

In the regeneration treatment of the Raney catalyst, further, it is necessary to add an alkali, preferably an inorganic alkali, e.g., a hydroxide or a carbonate of an alkali metal or a hydroxide or a carbonate of an alkali earth metal, or ammonia, to exert regeneration effects, as described above. The amount of the alkali added is in the range of usually 0.01 to 200% by weight, preferably 0.1 to 100% by weight, based on the amount of the catalyst, though it depends on the regeneration conditions.

The activation treatment and the regeneration treatment of the Raney catalyst may be continuously carried out with feeding a hydrogen gas or a hydrogen-containing mixed gas under pressure to the system, or they may be batchwise carried out in the system pressurized with a hydrogen gas.

Examples of the solvents include alcohol solvents, ether solvents of aliphatic and alicyclic hydrocarbons, and saturated aliphatic and alicyclic hydrocarbon solvents. These solvents can be used singly or in combination of two or more kinds. A mixed solvent containing one or more of these solvents and another solvent is also employable. Of these, preferable are solvents containing alcohol solvents (e.g., a solvent containing methanol), and particularly preferable is methanol. There is no specific limitation on the amount of the solvent used, but the amount thereof is in the range of usually 1 to 1,000 parts by weight, preferably 2 to 500 parts by weight, based on 1 part by weight of the Raney catalyst.

The period of time necessary for activating or regenerating the Raney catalyst can be made shorter as the pressure (hydrogen partial pressure) is increased, and it tends to become longer as the pressure is decreased. For example, when the pressure (hydrogen partial pressure) is 50 kg/cm$^2$, a period of about 10 minutes is necessary. When the pressure is 1 kg/cm$^2$, a period of about several tens hours is necessary. However, the time varies depending on the type of the Raney catalyst to be activated or regenerated, the conditions, and the type and the amount of alkali added in the regeneration treatment.

Preparation of Cyano Group-Containing Aromatic Methylamine from Aromatic Dinitrile In the present invention, an aromatic dinitrile is subjected to hydrogen reduction (hydrogenation) in the presence of the activated Raney catalyst mentioned above to prepare a cyano group-containing aromatic methylamine.

Firstly, the aromatic dinitrile subjected to the hydrogenation treatment is described below.

Aromatic Dinitrile

The aromatic dinitrile for use in the invention is a compound wherein two of hydrogen atoms bonded to the aromatic ring are substituted with nitrile groups (N≡C—). Examples of the aromatic rings include a benzene ring, a naphthalene ring and an anthracene ring. One or more of these aromatic rings may be bonded in the form of a chain (e.g., biphenyl), and the residual hydrogen atoms bonded to the aromatic rings may be substituted with halogen atoms, alkyl groups (preferably having about 1 to 5 carbon atoms), alkoxy groups (preferably having about 1 to 5 carbon atoms) or the like. Of the aromatic dinitriles, preferable are those having one benzene ring or one naphthalene ring, and more preferable are dicyanobenzene and dicyanonaphthalene each of which has only two nitrile groups as substituents.

Examples of the aromatic dinitriles preferably used include:

dicyanobenzenes, such as phthalonitrile, isophthalonitrile and terephthalonitrile; and dicyanonaphthalenes, such as 1,3-dicyanonaphthalene, 1,4-dicyanonaphthalene, 1,5-dicyanonaphthalene, 1,6-dicyanonaphthalene, 2,3-dicyanonaphthalene, 2,6-dicyanonaphthalene and 2,7-dicyanonaphthalene.

Of these, particularly preferable are phthalonitrile, isophthalonitrile and terephthalonitrile of the dicyanobenzenes. In the invention, the aromatic dinitrile may further have substituents in addition to the above-mentioned two nitrile groups. Examples of the substituents include halogen atoms, such as fluorine and chlorine; alkyl groups (preferably having about 1 to 5 carbon atoms), such as methyl and ethyl; and alkoxy groups (preferably having about 1 to 5 carbon atoms), such as methoxy and ethoxy. Specifically, 2-chloroterephthalonitrile, 2-chloro-4-methylisophthalonitrile or the like is also employable.

Hydrogenation of Aromatic Dinitrile

Preferred conditions of the hydrogen reduction (hydrogenation) reaction of the aromatic dinitrile are described below.

As the Raney catalyst, at least one of the activated Raney catalyst and the regenerated Raney catalyst mentioned above is used. The activated Raney catalyst is used in an amount of usually 0.1 to 10% by weight, preferably 0.5 to 5% by weight, based on the aromatic dinitrile subjected to hydrogenation (hydrogen addition), and the regenerated Raney catalyst is used in an amount of usually 0.1 to 50% by weight, preferably 0.5 to 20% by weight, based on the aromatic dinitrile subjected to hydrogenation (hydrogen addition).

When the activated Raney catalyst and/or the regenerated Raney catalyst is used in the above amount, a cyano group-containing aromatic methylamine wherein only one of the two nitrile groups of the aromatic dinitrile is hydrogenated can be obtained in a high yield. If the total amount of the catalysts is less than 0.1 % by weight, the rate of reaction becomes markedly slow. If the amount of the activated Raney catalyst exceeds 10% by weight, a diamine wherein the two nitrile groups of the aromatic dinitrile are both hydrogenated tends to be produced in a large amount, and thereby the yield of the cyano group-containing aromatic methylamine is decreased. Even if the total amount of the Raney catalysts exceeds 70% by weight based on the aromatic dinitrile subjected to hydrogenation (hydrogen addition), the rate of reaction hardly varies and no conspicuous difference in the yield of the cyano group-containing aromatic methylamine is observed, in comparison with the case of the total amount of 70% by weight.

In the present invention, in order to increase the yield of the cyano group-containing aromatic methylamine, at least one of iron, iron oxide and iron hydroxide can be allowed to be present together with the activated Raney catalyst and/or the regenerated Raney catalyst in the hydrogenation reaction of the aromatic dinitrile.

Examples of the iron, iron oxide and iron hydroxide preferably used include electrolytic iron, reduced iron, ferrous oxide, ferric oxide, iron oxyhydroxide, and iron supported on carriers (e.g., iron supported on alumina, iron supported on silica). The iron, iron oxide and iron hydroxide allowed to be present are used in the total amount of usually 0.01 to 200% by weight (in terms of iron component in case of iron supported on carrier), preferably 0.1 to 100% by weight, based on the amount of the Raney catalyst.

When the iron, iron oxide and iron hydroxide are used in the total amount of the above range, a cyano group-containing aromatic methylamine wherein only one of the two nitrile groups of the aromatic dinitrile is hydrogenated can be obtained in a high yield. If the total amount of the iron, iron oxide and iron hydroxide is less than 0.01% by weight based on the amount of the Raney catalyst, the effect of the yield improvement is not exerted. Even if the iron, iron oxide and iron hydroxide are allowed to be present in the total amount of more than 200% by weight, no conspicuous difference in the yield of the cyano group-containing aromatic methylamine is observed, in comparison with the case of the total amount of 200% by weight.

In the hydrogenation reaction of the aromatic dinitrile, a solvent can be generally employed. Examples of the solvents preferably used include alcohol solvents, ether solvents of aliphatic and alicyclic hydrocarbons, and saturated aliphatic and alicyclic hydrocarbon solvents.

These solvents can be used singly or as a mixed solvent containing any of these solvents. Preferably used are alcohol solvents or mixed solvents containing alcohol solvents. Particularly preferably used is methanol.

The solvent for use in the hydrogenation reaction of the aromatic dinitrile does not always need to be identical with the solvent for use in the activation (hydrogen treatment) or the regeneration of the Raney catalyst, but if the same solvent is used for the activation or the regeneration of the catalyst and for the hydrogenation reaction of the aromatic dinitrile, there is a great advantage in that replacement of the solvent is unnecessary.

The solvent is used in an amount of usually 1 to 30 parts by weight, preferably 1.5 to 10 parts by weight, based on 1 part by weight of the substance to be hydrogenated (i.e., aromatic dinitrile).

In the present invention, in order to restrain side reaction and thereby improve selectivity, an alkali, preferably an inorganic alkali, e.g., a hydroxide or a carbonate of an alkali metal or a hydroxide or a carbonate of an alkali earth metal, or ammonia can be added in the hydrogenation reaction of the aromatic dinitrile. The amount thereof depends on the reaction conditions, but for example, a hydroxide of an alkali metal is used in an amount of usually 0.01 to 200% by weight based on the amount of the catalyst.

In the present invention, the hydrogenation reaction of the aromatic dinitrile can be carried out at a temperature of usually room temperature (15 to 25° C.) to 200° C., preferably 50 to 130° C. Under the temperature conditions of lower than room temperature, a sufficient rate of the hydrogenation reaction is not obtained. Even if the hydrogenation reaction is carried out under the temperature conditions of higher than 200° C, no conspicuous superiority in the reaction rate, the yield and the selectivity is observed. The pressure in the hydrogenation reaction is desired to be in the range of usually 1 to 100 kg/cm$^2$, preferably 2 to 30 kg/cm$^2$, in terms of hydrogen partial pressure.

The hydrogen gas for use in the invention does not always need to be of high purity, and the hydrogen gas may contain another gas so far as it exerts no particular influence on the hydrogenation reaction. For example, an inert gas may be contained.

It is desired that the hydrogenation reaction is completed at the time when the hydrogen is absorbed by the reaction system in the theoretical amount or thereabout, namely 100 to 120% of the theoretical amount, preferably 100 to 110% thereof.

Through the hydrogenation reaction of the aromatic dinitrile, only one of the two nitrile groups (N≡C—) of the aromatic dinitrile is converted to "$H_2N-H_2C-$" (aminomethyl group) in high efficiency, and a cyano group-containing aromatic methylamine having one nitrile group and one aminomethyl group can be obtained.

In the present invention, the conversion ratio of the aromatic dinitrile varies depending on the type of the catalyst, etc. and is not decided indiscriminately, but it is usually not less than 90% by mol, preferably not less than 95% by mol, and the yield of the cyano group-containing aromatic methylamine is usually not less than 70%, preferably not less than 75%.

EFFECT OF THE INVENTION

According to the present invention, hydrogen reduction of the aromatic dinitrile is carried out in the presence of at least one of the activated Raney catalyst (preferably Raney catalyst activated in a solvent in a hydrogen atmosphere and containing nickel and/or cobalt) and the regenerated Raney catalyst (preferably Raney catalyst regenerated in a solvent in a hydrogen atmosphere and in the presence of an alkali and containing nickel and/or cobalt) in the below-described amount, particularly preferably in the presence of the above Raney catalyst and at least one of iron, iron oxide and iron hydroxide in an amount of 0.1 to 100% by weight based on the Raney catalyst, whereby the aromatic dinitrile is reacted at a high conversion ratio under the conditions of a low temperature and a low pressure, with restraining production of a diamine wherein two nitrile groups of the aromatic dinitrile are both hydrogenated. In the hydrogen reduction of the aromatic dinitrile, the activated Raney catalyst is used in an amount of preferably 0.1 to 10% by weight, more preferably 0.5 to 5% by weight, based on the aromatic dinitrile, and the regenerated Raney catalyst is used in an amount of preferably 0.1 to 50% by weight, more preferably 0.5 to 20% by weight, based on the aromatic dinitrile. By the above hydrogenation, a cyano group-containing aromatic methylamine wherein only one of the two nitrile groups is hydrogenated can be prepared in a high yield.

EXAMPLE

The present invention is further described with reference to the following examples, but it should be construed that the invention is in no way limited to those examples.

Example 1

Activation of Catalyst

To a 500 ml autoclave, 180 ml of methanol and 2.0 g of a Raney nickel catalyst R-2400 (available from W. R. Grace Co.) were introduced. Then, stirring and heating of the contents of the autoclave were started at room temperature (24° C.) under a hydrogen pressure of 5 kg/cm$^2$ (gauge pressure, the same shall apply hereinafter), and the contents of the autoclave were maintained at 100° C. for 2 hours. The maximum pressure during the heating was 9 kg/cm$^2$. The contents of the autoclave were cooled to room temperature. Then, the catalyst was precipitated and recovered.

Hydrogenation Reaction

To a 500 ml autoclave, 180 ml of methanol, 1.0 g of the activated Raney nickel obtained above, 50 g of terephthalonitrile and 0.2 g of sodium hydroxide were introduced. Then, stirring and heating of the contents of the autoclave were started at ordinary temperature under a hydrogen pressure of 10 kg/cm$^2$ to initiate hydrogenation reaction of the terephthalonitrile. The temperature of the system was maintained at 100° C., and the flow rate of hydrogen was monitored by a thermal mass flow meter (manufactured by Kojima Seisakusho). When the amount of hydrogen absorbed reached 105% of the theoretical value, the reaction was completed. The reaction product obtained was cooled to room temperature. Then, the catalyst was separated and removed by filtration, and the reaction liquid obtained was analyzed by a gas chromatography internal standard method. As a result, the conversion ratio of the terephthalonitrile was not less than 90% by mol, the yield of p-cyanobenzylamine was 80%, and the yield of p-xylenediamine was 5%.

Comparative Example 1

To a 500 ml autoclave, 180 ml of methanol, 1.0 g of a Raney nickel catalyst R-2400 (available from W.R. Grace Co.) having been subjected to no activation treatment (hydrogen treatment), 50 g of terephthalonitrile and 0.2 g of sodium hydroxide were introduced. Then, stirring and heating of the contents of the autoclave were started at ordinary temperature under a hydrogen pressure of 10 kg/cm$^2$ to initiate hydrogenation reaction of the terephthalonitrile. The temperature of the system was maintained at 100° C., and the flow rate of hydrogen was monitored. When the amount of hydrogen absorbed reached 88% of the theoretical value, the progress of the reaction stopped. Then, the reaction liquid was cooled to room temperature. As a result, unreacted terephthalonitrile remained in the reaction liquid. The unreacted terephthalonitrile was removed by filtration together with the catalyst, and the reaction liquid obtained was analyzed by a gas chromatography internal standard method. As a result, the yield of p-cyanobenzylamine was 47%, and the yield of p-xylenediamine was 2%. From the weight of the terephthalonitrile filtered and the analysis of the reaction liquid by the gas chromatography internal standard method, the conversion ratio of the terephthalonitrile proved to be 68% by mol.

Example 2

Regeneration of Catalyst

To a 500 ml autoclave, 180 ml of methanol, about 1.0 g of a Raney nickel catalyst having been used for hydrogenation reaction of terephthalonitrile under the same conditions as in Example 1 and recovered by separation after completion of the reaction, and 0.2 g of sodium hydroxide were introduced. Then, stirring and heating of the contents of the autoclave were started at room temperature (24° C.) under a hydrogen pressure of 5 kg/cm$^2$, and the contents of the autoclave were maintained at 100° C. for 2 hours. The maximum pressure during the heating was 7 kg/cm$^2$. Then, the contents of the autoclave were cooled to room temperature.

Hydrogenation Reaction

To a 500 ml autoclave containing the regenerated Raney nickel catalyst obtained above, 50 g of terephthalonitrile was added. Then, stirring and heating of the contents of the autoclave were started at ordinary temperature under a hydrogen pressure of 10 kg/cm$^2$ to initiate hydrogenation reaction of the terephthalonitrile. The temperature of the system was maintained at 100° C., and the flow rate of hydrogen was monitored. When the amount of hydrogen absorbed reached 105% of the theoretical value, the reaction was completed. The reaction product obtained was cooled to room temperature. Then, the catalyst was separated and removed by filtration, and the reaction liquid obtained was analyzed by a gas chromatography internal standard method. As a result, the conversion ratio of the terephthalonitrile was not less than 99% by mol, the yield of p-cyanobenzylamine was 77%, and the yield of p-xylenediamine was 5%.

Comparative Example 2

Regeneration of Catalyst

Regeneration of a catalyst was carried out under the same conditions as in Example 2, except that sodium hydroxide was not introduced.

Hydrogenation Reaction

Hydrogenation reaction of terephthalonitrile was carried out in the presence of the catalyst obtained above under the same conditions as in Example 2. The reaction product was cooled to room temperature. Then, the catalyst was filtered out, and the reaction liquid obtained was analyzed by a gas chromatography internal standard method. As a result, the conversion ratio of the terephthalonitrile was not less than 99% by mol, but the yield of p-cyanobenzylamine was 63%, and the yield of p-xylenediamine was 6%.

Example 3

Activation of Catalyst

Activation of a catalyst was carried out in the same manner as in Example 1.

Regeneration of Catalyst

Regeneration of a catalyst was carried out in the same manner as in Example 2.

Hydrogenation Reaction

To a 500 ml autoclave containing the regenerated Raney nickel catalyst obtained above, 0.5 g of the activated Raney catalyst and 50 g of terephthalonitrile were added. Then, stirring and heating of the contents of the autoclave were started at ordinary temperature under a hydrogen pressure of 10 kg/cm$^2$ to initiate hydrogenation reaction of the terephthalonitrile. The temperature of the system was maintained at 100° C., and the flow rate of hydrogen was monitored. When the amount of hydrogen absorbed reached 105% of the theoretical value, the reaction was completed. The reaction product obtained was cooled to room temperature. Then, the catalyst was separated and removed by filtration, and the reaction liquid obtained was analyzed by a gas chromatography internal standard method. As a result, the conversion ratio of the terephthalonitrile was not less than 99% by mol, the yield of p-cyanobenzylamine was 79%, and the yield of p-xylenediamine was 5%.

Example 4

Activation of Catalyst

Activation of a catalyst was carried out in the same manner as in Example 1.

Hydroaenation Treatment

Together with 1.0 g of the activated Raney nickel catalyst obtained above, 0.2 of reduced iron, 50 g of terephthalonitrile and 0.2 g of sodium hydroxide were introduced in the same manner as in Example 1, and hydrogenation reaction of the terephthalonitrile was carried out under the same conditions as in Example 1. The reaction product was cooled to room temperature. Then, the catalyst and the reduced iron were filtered out, and the reaction liquid obtained was analyzed by a gas chromatography internal standard method. As a result, the conversion ratio of the terephthalonitrile was not less than 99% by mol, the yield of p-cyanobenzylamine was 85%, and the yield of p-xylenediamine was 4%.

Example 5

Regeneration of Catalyst

To a 500 ml autoclave, 180 ml of methanol, about 1.2 g (total amount) of the Raney nickel catalyst and the reduced iron both having been used for hydrogenation reaction of terephthalonitrile and recovered by separation after completion of the reaction in Example 4, and 0.2 g of sodium hydroxide were introduced. Then, stirring and heating of the contents of the autoclave were started at room temperature (24° C.) under a hydrogen pressure of 5 kg/cm$^2$ (gauge pressure, the same shall apply hereinafter), and the contents of the autoclave were maintained at 100° C. for 2 hours. The maximum pressure during the heating was 6.7 kg/cm$^2$. Then, the contents of the autoclave were cooled to room temperature.

Hydrogenation Reaction

To a 500 ml autoclave containing the regenerated Raney nickel catalyst obtained above, 50 g of terephthalonitrile was added, and hydrogenation reaction of the terephthalonitrile was carried out under the same conditions as in Example 1. The reaction product was cooled to room temperature. Then, the catalyst and the reduced iron were filtered out, and the reaction liquid obtained was analyzed by a gas chromatography internal standard method. As a result, the conversion ratio of the terephthalonitrile was not less than 99% by mol, the yield of p-cyanobenzylamine was 83%, and the yield of p-xylenediamine was 5%.

Example 6

Activation of Catalyst

A catalyst was activated under the same conditions as in Example 1, except that methanol used for activation of the catalyst was replaced with ethanol.

Hydrogenation Reaction

Hydrogenation reaction of terephthalonitrile was carried out under the same conditions as in Example 1. The reaction product was cooled to room temperature. Then, the catalyst was filtered out, and the reaction liquid obtained was analyzed by a gas chromatography internal standard method. As a result, the conversion ratio of the terephthalonitrile was not less than 99% by mol, the yield of p-cyanobenzylamine was 77%, and the yield of p-xylenediamine was 5%.

Example 7

Activation of Catalyst

Activation of a catalyst was carried out in the same manner as in Example 1.

Hydrogenation Reaction

Hydrogenation reaction of isophthalonitrile was carried out under the same conditions as in Example 1, except that the terephthalonitrile was replaced with isophthalonitrile. The reaction product was cooled to room temperature. Then, the catalyst was filtered out, and the reaction liquid obtained was analyzed by a gas chromatography internal standard method. As a result, the conversion ratio of the isophthalonitrile was not less than 99% by mol, the yield of m-cyanobenzylamine was 82%, and the yield of m-xylenediamine was 6%.

Example 8

Activation of Catalyst

Activation of a catalyst was carried out in the same manner as in Example 1.

Hydrogenation Reaction

Hydrogenation reaction of terephthalonitrile was carried out under the same conditions as in Example 1, except that the amount of the catalyst was varied to 1.5 g. The reaction product was cooled to room temperature. Then, the catalyst was filtered out, and the reaction liquid obtained was analyzed by a gas chromatography internal standard method. As a result, the conversion ratio of the terephthalonitrile was not less than 99% by mol, the yield of p-cyanobenzylamine was 79%, and the yield of p-xylenediamine was 5%.

Reference Example 1

To a 500 ml autoclave, 180 ml of methanol, about 1.0 g of a Raney nickel catalyst having been used for hydrogenation reaction of terephthalonitrile under the same conditions as in Example 1 and recovered by separation after completion of the reaction but not subjected to regeneration treatment, 50 g of terephthalonitrile and 0.2 g of sodium hydroxide were introduced. Then, stirring and heating of the contents of the autoclave were started at ordinary temperature under a hydrogen pressure of 10 kg/cm$^2$ to initiate hydrogenation reaction of the terephthalonitrile. The temperature of the system was maintained at 100° C., and the flow rate of hydrogen was monitored. When the amount of hydrogen absorbed reached 105% of the theoretical value, the reaction was completed. The reaction product obtained was cooled to room temperature. Then, the catalyst was separated and removed by filtration, and the reaction liquid obtained was analyzed by a gas chromatography internal standard method. As a result, the conversion ratio of the terephthalonitrile was not less than 99% by mol, but the yield of p-cyanobenzylamine was 58%, and the yield of p-xylenediamine was 3%.

Reference Example 2

Activation of Catalyst

Activation of a catalyst was carried out in the same manner as in Example 1.

Hydrogenation Reaction

Hydrogenation reaction of terephthalonitrile was carried out in the same manner as in Example 1, except that the amount of the catalyst was varied to 0.02 g and the amount of sodium hydroxide was varied to 0.005 g. As a result, absorption of hydrogen hardly took place. The conversion ratio of the terephthalonitrile was less than 1% by mol.

Reference Example 3

Activation of Catalyst

Activation of a catalyst was carried out in the same manner as in Example 1.

Hydrogenation Reaction

Hydrogenation reaction of terephthalonitrile was carried out under the same conditions as in Example 1, except that the amount of the catalyst was varied to 10 g, the reaction pressure (hydrogen pressure) was varied to 5.0 kg/cm$^2$, and the reaction temperature was varied to 60° C.

Then, the temperature of the system was lowered to room temperature. Thereafter, the catalyst was filtered out, and the reaction liquid obtained was analyzed by a gas chromatography internal standard method. As a result, the conversion ratio of the terephthalonitrile was not less than 99% by mol, the yield of p-cyanobenzylamine was 73%, and the yield of p-xylenediamine was 17%.

What is claimed is:

1. A process for preparing a cyano group-containing aromatic methylamine from an aromatic dinitrile, said process using, as a catalyst, a Raney catalyst activated by bringing it into contact with hydrogen in a solvent.

2. A process for regenerating a Raney catalyst, comprising bringing a Raney catalyst having been used for preparing a cyano group-containing aromatic methylamine from an aromatic dinitrile into contact with hydrogen in a solvent in the presence of an alkali.

3. A process for preparing a cyano group-containing aromatic methylamine from an aromatic dinitrile, said process using, as a catalyst, a Raney catalyst regenerated by the process as claimed in claim 2.

4. The process as claimed in claim 1 or 3, wherein the activated Raney catalyst is used in an amount of 0.1 to 10% by weight based on the aromatic dinitrile, and/or the regenerated Raney catalyst is used in an amount of 0.1 to 50% by weight based on the aromatic dinitrile.

5. The process as claimed in claim 1 or 3, wherein the activated Raney catalyst is used in an amount of 0.5 to 5% by weight based on the aromatic dinitrile, and/or the regenerated Raney catalyst is used in an amount of 0.5 to 20% by weight based on the aromatic dinitrile.

6. The process as claimed in claim 1, wherein the activated Raney catalyst is one obtained by activating a Raney catalyst under the conditions of a temperature of room temperature to 200° C. and a hydrogen partial pressure of 0.1 to 50 kg/cm.

7. A process for regenerating a Raney catalyst, comprising bringing a Raney catalyst having been used for preparing a cyano group-containing aromatic methylamine from an aromatic dinitrile into contact with hydrogen in a solvent in the presence of an alkali, wherein the regenerated Raney catalyst is one obtained by regenerating a Raney catalyst having been used for preparing a cyano group-containing aromatic methylamine from an aromatic dinitrile, under the conditions of a temperature of room temperature to 200° C. and a hydrogen partial pressure of 0.1 to 50 kg/cm$^2$ in the presence of an alkali in an amount of 0.1 to 100% by weight based on the Raney catalyst subjected to the regeneration.

8. The process as claimed in any one of claims 1 to 3, wherein at least one of iron, iron oxide and iron hydroxide is allowed to be present together with the activated Raney catalyst and/or the regenerated Raney catalyst.

9. The process as claimed in claim 8, wherein at least one of iron, iron oxide and iron hydroxide is used in an amount of 0.1 to 100% by weight based on the Raney catalyst.

10. The process as claimed in any one of claims 1 to 3, wherein the Raney catalyst is one containing nickel and/or cobalt.

11. The process as claimed in any one of claims 1 to 3, wherein the Raney catalyst is Raney nickel or modified Raney nickel.

12. The process as claimed in any one of claims 1 to 3, wherein the solvent contains an alcohol.

13. The process as claimed in any one of claims 1 to 3, wherein the solvent is methanol.

14. The process as claimed in any one of claims 1 to 3, wherein the aromatic dinitrile is at least one of phthalonitrile, isophthalonitrile and terephthalonitrile.

15. The process as claimed in claim 4, wherein the activated Raney catalyst is one obtained by activating a Raney catalyst under the conditions of a temperature of room temperature to 200° C. and a hydrogen partial pressure of 0.1 to 50 kg/cm$^2$.

16. The process as claimed in 5, wherein the activated Raney catalyst is one obtained by activating a Raney catalyst under the conditions of a temperature of room temperature to 200° C. and a hydrogen partial pressure of 0.1 to 50 kg/cm$^2$.

17. The process as claimed in claim 3, wherein the regenerated Raney catalyst is one obtained by regenerating a Raney catalyst having been used for preparing a cyano group-containing aromatic methylamine from an aromatic dinitrile, under the conditions of a temperature of room temperature to 200° C. and a hydrogen partial pressure of 0.1 to 50 kg/cm$^2$ in the presence of an alkali in an amount of 0.1 to 100% by weight based on the Raney catalyst subjected to the regeneration.

18. The process as claimed in claim 4, wherein the regenerated Raney catalyst is one obtained by regenerating a Raney catalyst having been used for preparing a cyano group-containing aromatic methylamine from an aromatic dinitrile, under the conditions of a temperature of room temperature to 200° C. and a hydrogen partial pressure of 0.1 to 50 kg/cm$^2$ in the presence of an alkali in an amount of 0.1 to 100% by weight based on the Raney catalyst subjected to the regeneration.

19. The process as claimed in claim 5, wherein the regenerated Raney catalyst is one obtained by regenerating a Raney catalyst having been used for preparing a cyano group-containing aromatic methylamine from an aromatic dinitrile, under the conditions of a temperature of room temperature to 200° C. and a hydrogen partial pressure of 0.1 to 50 kg/cm$^2$ in the presence of an alkali in an amount of 0.1 to 100% by weight based on the Raney catalyst subjected to the regeneration.

* * * * *